United States Patent

Wake et al.

[11] Patent Number: 6,029,077
[45] Date of Patent: Feb. 22, 2000

[54] DEVICE FOR DETERMINING THE PERIMETER OF THE SURFACE OF AN OBJECT BEING SCANNED AND FOR LIMITING REFLECTION FROM THE OBJECT SURFACE

[75] Inventors: Robert H. Wake, Sunrise; Richard J. Grable, Plantation, both of Fla.; David P. Rohler, University Heights, Ohio

[73] Assignee: Imaging Diagnostic Systems, Inc., Plantation, Fla.

[21] Appl. No.: 08/965,149

[22] Filed: Nov. 6, 1997

Related U.S. Application Data

[60] Provisional application No. 60/029,898, Nov. 8, 1996.

[51] Int. Cl.$^7$ ........................................................ A61B 5/00
[52] U.S. Cl. ........................ 600/407; 600/476; 600/587; 33/512; 33/554; 33/555
[58] Field of Search ..................................... 600/407, 473, 600/476, 587; 356/376; 250/559.19, 559.22; 33/511, 512, 546, 551, 553–555, 555.1

[56] References Cited

U.S. PATENT DOCUMENTS

| | | |
|---|---|---|
| 4,400,784 | 8/1983 | Hacskaylo . |
| 4,679,331 | 7/1987 | Koontz .................................. 33/551 |
| 4,810,875 | 3/1989 | Wyatt .................................... 600/476 |
| 4,995,170 | 2/1991 | Brule et al. ............................ 33/551 |
| 5,148,022 | 9/1992 | Kawaguchi et al. . |
| 5,353,799 | 10/1994 | Chance . |
| 5,376,796 | 12/1994 | Chan et al. . |
| 5,384,573 | 1/1995 | Turpin . |
| 5,386,447 | 1/1995 | Siczek . |
| 5,409,497 | 4/1995 | Siczek et al. . |
| 5,411,024 | 5/1995 | Thomas et al. . |
| 5,426,685 | 6/1995 | Pellegrino et al. . |
| 5,432,703 | 7/1995 | Clynch et al. . |
| 5,439,000 | 8/1995 | Gunderson et al. . |
| 5,471,541 | 11/1995 | Burtnyk et al. . |
| 5,477,051 | 12/1995 | Tsuchiya . |
| 5,477,371 | 12/1995 | Shafir . |
| 5,506,683 | 4/1996 | Yang et al. . |
| 5,530,652 | 6/1996 | Croyle et al. . |
| 5,555,885 | 9/1996 | Chance . |

*Primary Examiner*—Ruth S. Smith
*Attorney, Agent, or Firm*—Shlesinger, Arkwright & Garvey LLP

[57] ABSTRACT

An apparatus for determining the perimeter of an object being scanned comprises a movable arm adapted to follow the surface of an object being scanned as the arm is orbited around the object; the arm having one end being adapted to maintain contact with the surface as the arm is orbited around the object; and an encoder operably connected to the arm for determining the movement of the lever arm at each angular position around the object. An opaque cup is positioned at one end of the lever arm immediately over a point on said surface at which a laser beam impinges on the surface of the object being scanned such that reflection from the surface is retained within the cup.

16 Claims, 4 Drawing Sheets

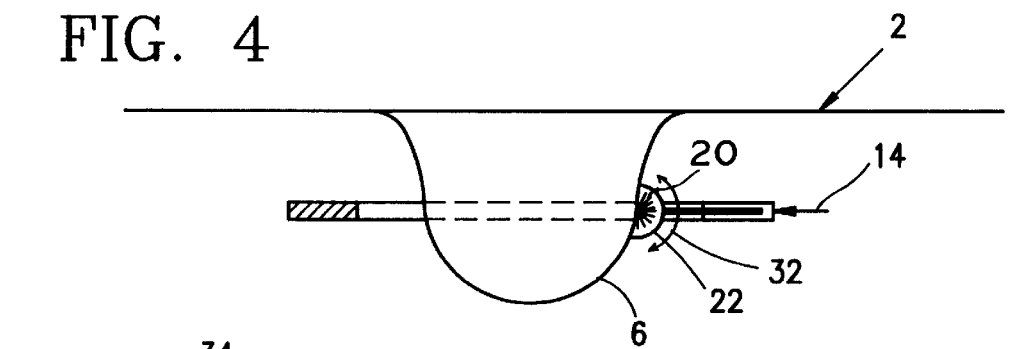
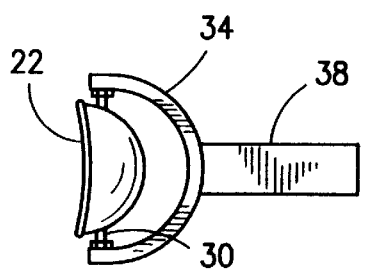
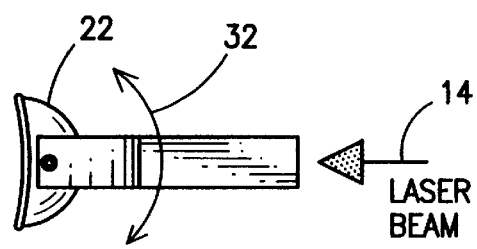
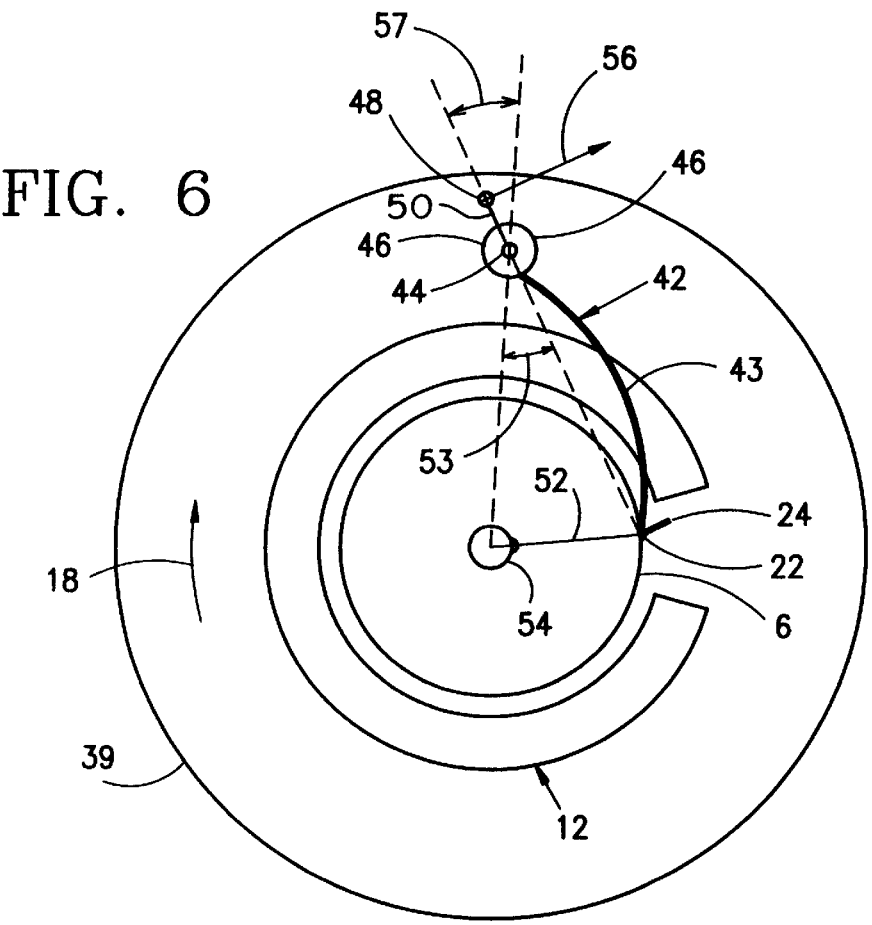

DEVICE FOR DETERMINING THE PERIMETER OF THE SURFACE OF AN OBJECT BEING SCANNED AND FOR LIMITING REFLECTION FROM THE OBJECT SURFACE

RELATED APPLICATION

This application claims the priority benefit of provisional application Ser. No. 60/029,898, filed on Nov. 8, 1996, and is related to provisional application Ser. No. 60/029,897, filed on Nov. 8, 1996, both of which are hereby incorporated by reference.

This application is also related to copending application Ser. No. 08/484,904, filed Jun. 7, 1995, now U.S. Pat. No. 5,692,511, issued Dec. 2, 1997, which is hereby incorporated by reference.

FIELD OF THE INVENTION

The present invention relates generally to a diagnostic medical imaging apparatus that employs a near-infrared laser as a radiation source and more particularly to a device for determining the perimeter of the surface of the tissue being scanned and preventing any reflected light from the scanned surface from scattering inside the scanning chamber.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammograms 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested, as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This techniques is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomena causes the light photons to scatter inside the tissue before the photons emerge out of the scanned sample.

In addition to in vivo scattering, a significant percentage of the impinging laser beam is reflected off of the surface of the tissue being scanned. The reflected photons significantly raise the ambient light level in the otherwise enclosed scanning chamber. It is important that the scanning chamber be free of extraneous light so that the detectors only see light that had passed through the tissue. The ability to reduce the reflection off of interior surfaces of the scanning chamber is somewhat limited because techniques that prove to be highly successful at one wavelength do not necessarily prove effective at other wavelengths.

In optical tomography, mathematical formulas and projections techniques have been devised to perform a reconstruction function somewhat similar to x-ray tomography. However, because light photon propagation is not a straight line, techniques to produce cross-section images are mathematically intensive and invariably require establishing the boundary of the scanned object. Boundary determination is important because it serves as the basis for reconstruction techniques to produce interior structure details. Algorithms to date do not use any form of direct measurement techniques to establish the boundary of the scanned object.

OBJECTS AND SUMMARY OF THE INVENTION

It is an object of the present invention to provide a device for limiting light reflection from the surface of the object being scanned to limit the detectors to only see light that has passed through the object.

It is another object of the present invention to provide a device for bringing a laser beam immediately over the point at which the laser beam impinges on the surface of the object being scanned, thereby minimizing any reflection from the surface.

It is still another object of the present invention to provide a device that captures reflected light from the surface of the object being scanned, thereby minimizing the detection of light that had not passed through the object.

It is another of the present invention to provide a laser beam delivery device that makes contact with the surface of the object being scanned without deforming the perimeter of the surface of the object.

It is still another object of the present invention to provide a device for mapping the perimeter of the object being scanned.

In summary, the present invention provides an apparatus for determining the perimeter of an object being scanned comprises a movable arm adapted to follow the surface of an object being scanned as the arm is orbited around the object; the arm having one end being adapted to maintain contact with the surface as the arm is orbited around the object; and an encoder operably connected to the arm for determining the movement of the lever arm at each angular position around the object. An opaque cup is positioned at one end of the lever arm immediately over a point on said surface at which a laser beam impinges on the surface of the object being scanned such that reflection from the surface is retained within the cup.

These and other objects of the present invention will become apparent from the following detailed description.

BRIEF DESCRIPTIONS OF THE DRAWINGS

FIG. 4 is a schematic side elevational view of the scanning chamber of FIG. 1 showing the relative position of the breast and the laser beam delivery apparatus.

FIGS. 5A and 5B are enlarged schematic top plan and side elevational views of a cup used in the laser beam delivery device to trap the reflected radiation from the scanned surface.

FIG. 6 is a schematic top plan view of the scanning chamber of FIG. 1 showing a device for mapping the perimeter of the breast being scanned and for positioning the laser delivery device against the breast.

DETAILED DESCRIPTION OF THE INVENTION

Figure 1:
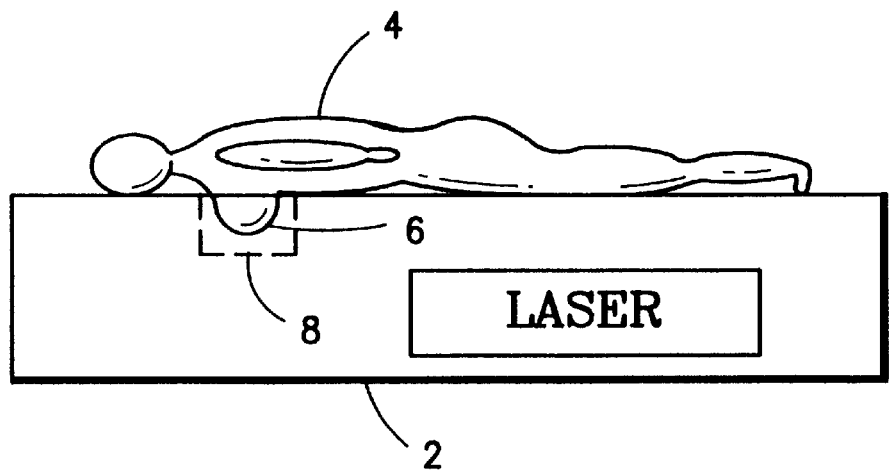
FIG. 1 is a schematic side elevational view of a laser imaging apparatus with a patient in a prone position with one of her breasts positioned within a scanning chamber for an optical tomographic study.

A scanning apparatus 2, such as that described in copending application Ser. No. 08/484,904, filed Jun. 7, 1995, now U.S. Pat. No. 5,692,511, issued Dec. 2, 1997, is schematically disclosed in FIG. 1. A patient 4 is positioned prone on a top surface of the apparatus 2 with her breast 6 disposed pendent within a scanning chamber 8. A laser beam from a laser source 10 is brought to the scanning chamber 8 to illuminate the breast 6.

Figure 2:
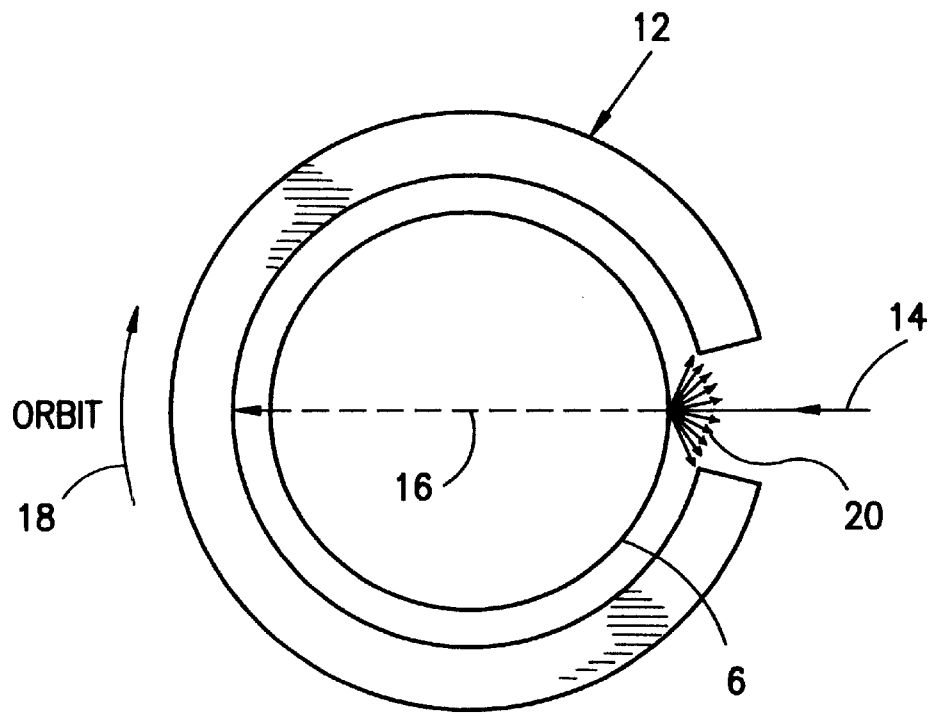
FIG. 2 is a schematic top view of the scanning chamber of FIG. 1.

Referring to FIG. 2, the scanning chamber 8 comprises of an array of detectors 12 disposed around the breast in an arc. A laser beam 14 is brought into the scanning chamber to impinge on the breast 6. A laser beam traversing through the breast 6 and exiting at the other side, as generally disclosed at 16, is picked up by one of the detectors 12. The laser beam 14 and the array of detectors 12 are moved in an orbit 18 around the breast 6 at equally spaced angular positions until a complete circle has been traversed. At each angular position, light detected by the array of detectors 12 is recorded for later use in reconstructing an image of the breast 6.

At the point at which the laser beam 14 impinges on the surface of the breast 6, a portion of the laser beam 14 enters the breast, such as that shown schematically at 16, and the rest of the beam is reflected off the surface, such as that shown schematically at 20. The reflected photons are undesirable, since they introduce unwanted noise in the image reconstruction process. The coverage of the reflected photons 20 is a solid angle of at least $2\pi$ steradians.

Figure 3:
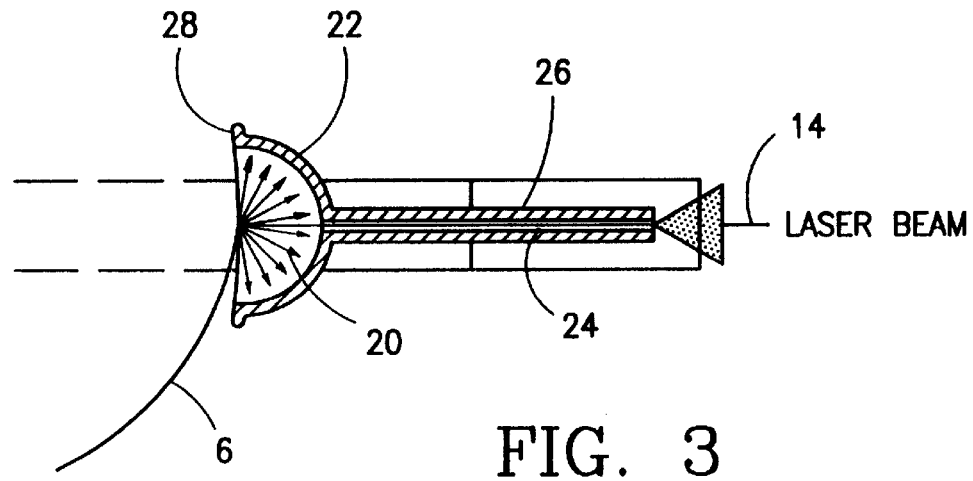
FIG. 3 is a schematic enlarged side elevational view of an apparatus for coupling the laser beam to the surface of the breast being scanned.

To alleviate the above problem, an opaque cup 22 is advantageously disposed at the point at which the laser beam impinges the breast surface, as best shown in FIG. 3. The laser beam 14 is carried by a fiber optic cable 24 enclosed within an opaque outer jacket 26. The end of the cable 24 is operably secured to the cup 22 so that the laser beam impinges the surface of the breast within the cup 22, thereby permitting the cup to capture the reflected light. The outer edge 28 of the cup 22 is radiused and polished to advantageously reduce the co-efficient of friction and minimize the drag of the cup against the scanned surface.

In order to avoid any misalignment of the cup 22 with the surface of the breast 6, a pivot 30 is advantageously provided to allow the cup 22 to rotate in the direction 32 to allow the cup 22 to remain in contact with the surface of the breast 6 at various points along the surface of the breast 6 and trap the reflected radiation 20, as best shown in FIGS. 4, 5A and 5B. The pivot 30 may be supported by a suitable structure, such as a Y-shaped structure 34. The end portion of the fiber optic cable 24 is operably connected to the cup 22 by standard means in such a way that the pivot 30 is not hampered.

An arrangement for supporting the cup 22 at the surface of the breast being scanned is disclosed in FIG. 6. An orbit plate 39 supports the array of detectors 12 and a swinging arm assembly 42 which is pivotable at 44. The assembly 42 includes a lever arm 43 at one end of which is secured the cup 22 and the fiber optic cable 24. A rotary encoder 46 is operably associated with the pivot 44. A weight 48 is attached by an arm 50 to the center of rotation of the lever arm 43 at pivot 44. The lever arm 43 has a range of motion, generally indicated by the distance 52 and angle 53, to allow scanning of an object with varying diameters, from the smallest shown at 54 to the largest shown at 6.

When the orbit plate 39 begins to rotate in the orbit direction 18, a velocity vector 56 is imparted to the weight 48, creating a torque on the rotary encoder arm 50 and the lever arm 43. The torque causes the cup 22 to press against the surface of the breast 6. By adjusting the weight 48 and the arm 50, the force acting on the cup 22 is varied to a desired level that is comfortable to the patient and without deforming the surface of the breast. Since the torque is continuously acting on the cup 22 to press it against the surface of the breast 6, the cup 22 will always stay pressed against the breast, from the smallest diameter to the largest diameter of the surface perimeter, as long as the orbit plate 39 is rotating around the breast.

When the orbit plate 39 is stationary, the lever arm 43 is moved away from the breast 6 by means of the action of the weight 48 due to gravity. The arm 50 holding the weight 48 is designed to allow the force of gravity to produce a torque on the lever arm 43 in the opposite direction to that produced when the orbit plate 39 is moving, thereby causing the arm 43 to move away from the breast when the orbit plate 39 is at rest. When the orbit plate 39 is moving, the torque produced by the weight 48 caused by gravity is less than and opposite to the torque produced by velocity vector 56, the net effect being a torque in the clockwise direction to bring the cup 22 in contact with the breast surface.

Figure 7:
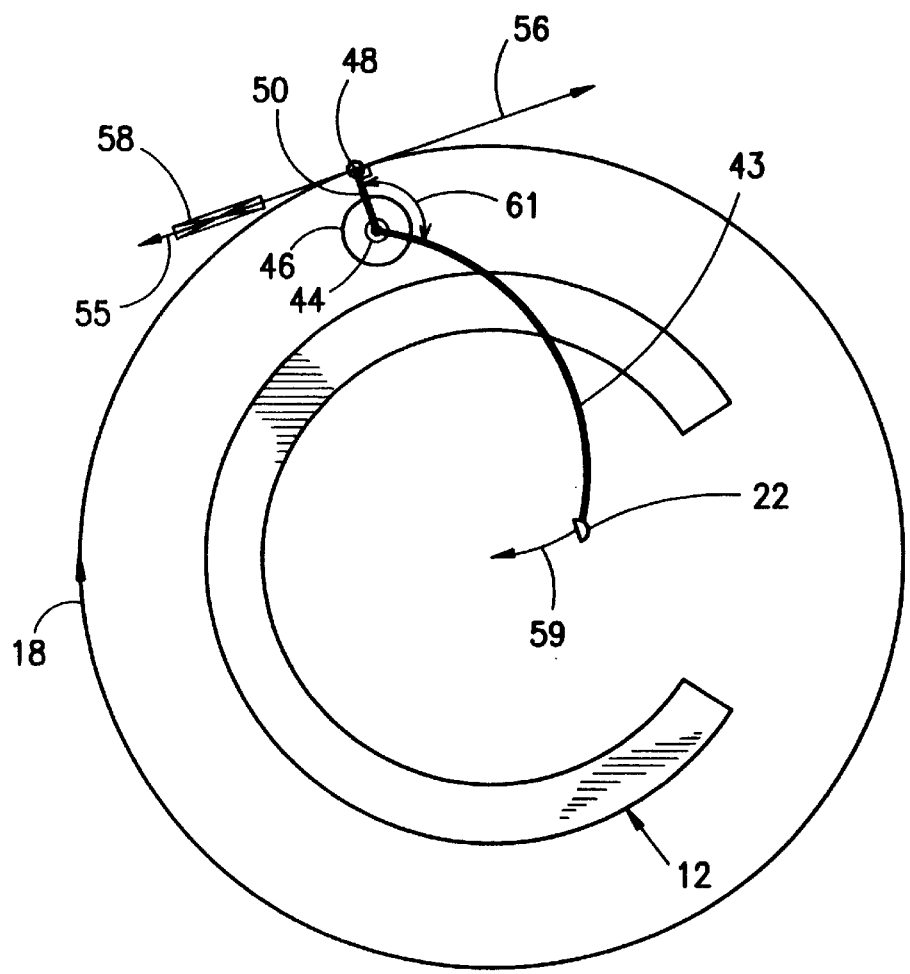
FIG. 7 is another embodiment of the arrangement of FIG. 6.

An alternative arrangement for producing a counter-clockwise torque for moving the lever arm 43 away from the breast surface when scanning is not being performed is to use a spring 58 to exert a counter-clockwise torque 55 on the arm 50 as best shown in FIG. 7. When the orbit plate 39 is stationary, the spring 58 acts on the weight 48 and the arm 50 to produce the counter-clockwise torque 55 about the pivot 44, thereby rotating the arm 43 counter-clockwise away from the breast surface. When the orbit plate 39 is rotating in the direction 18, the velocity vector 56 acting on the weight 48 produces a clockwise torque with the arm 50 about the pivot 44 thereby to rotate the lever arm 43 clockwise to bring the cup 22 in contact with the breast 6, generally indicated at 59. The torque produced by the velocity vector 56 is greater than and in the opposite direction to the torque produce by the spring 58 such that the net torque is in the clockwise direction, generally indicated at 61.

The rotary encoder 46 is designed to produce a signal in proportion to the number of degrees of rotation of the lever arm 43. As the arm assembly 42 is orbited around the breast 6, the position of the cup 22 at each pre-determined angular position around a complete circle is determined by the angular displacement 57 of the pivot 44, which is detected by the rotary encoder 48. A person of ordinary skill in the art will understand that at each angular position of the orbit, the radial distance of the cup 22 from a known reference point is uniquely determined from the angular displacement 57 of the arm 43 about the pivot 44. A trace of the periphery of the breast 6 is thus determined for each complete orbit of the arm assembly 42.

Figure 8:
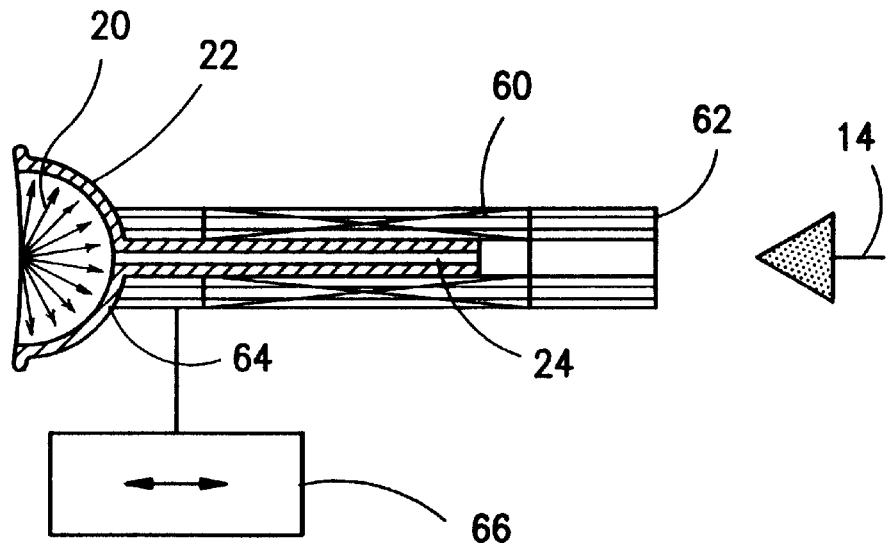
FIG. 8 is a schematic side elevational view of another embodiment of a device for obtaining the breast perimeter data during a scanning process.

Another embodiment for keeping cup 22 in contact with the breast 6 during the scanning process is disclosed in FIG. 8. The cup 22 is advantageously held against the surface of the breast 6 by means of a spring 60 pushing against a stationary block 62. Passageways 64 are provided to permit compressed air to be introduced inside the cup to counteract the pressure of the spring 60, thereby to adjust the pressure to the required level that the cup 22 exerts against the breast 6 during the scanning process. A linear encoder 66 operably secured to the cup 22 provides an electronic signal representative of the linear position of the cup 22 as it traverses the periphery of the breast at each angular position of the orbit. The spring constant for the spring 60 is selected to adjust the contact pressure of the cup 22 to the required level.

Figure 9:
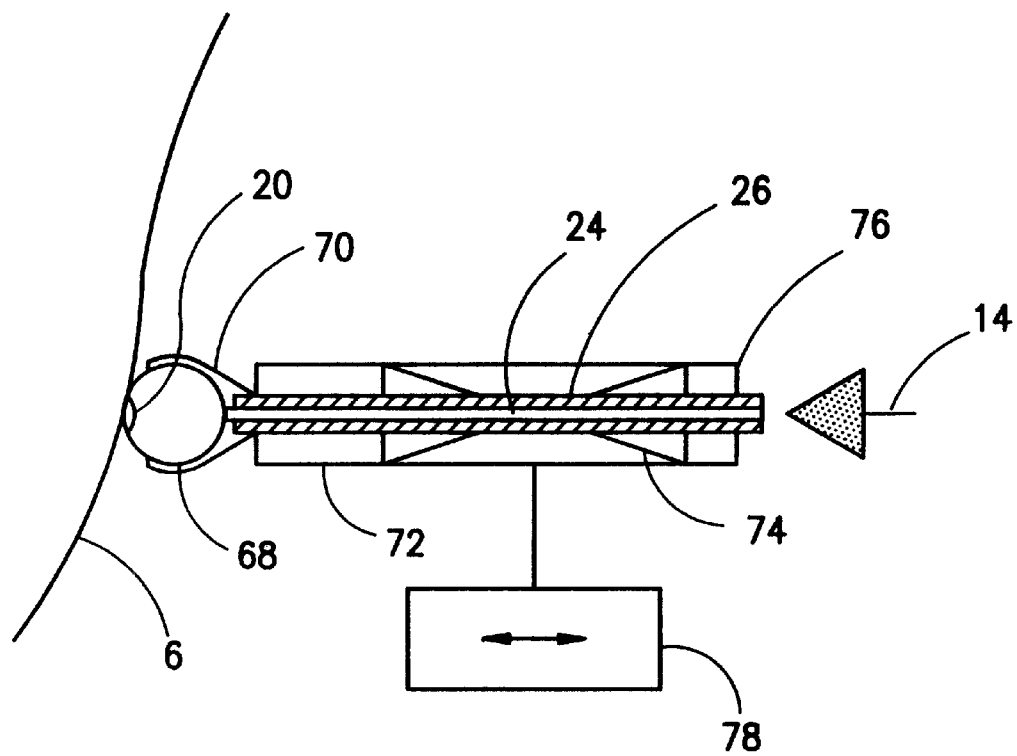
FIG. 9 is a schematic side elevational view of yet another embodiment of a device for obtaining the breast perimeter data during a scanning process.

Another embodiment of the present invention is disclosed in FIG. 9. A spherical lens 68 is used to couple the output of the fiber optic cable 24 into the breast 6. A housing 70 holds the spherical lens 68 and is operably secured to a slidable support block 72. A spring 74 presses against the block 72 and the stationary block 76, thereby pressing the spherical lens 68 against the breast 6. The spring constant of the spring 74 is selected to provide the desire tracking pressure on the breast. The lens 68 couples the laser beam from the fiber optic cable. Light reflection from the surface enters the lens and is trapped inside. The lens 68 advantageously rolls against the surface being scanned, thereby minimizing friction. A linear encoder 78 operably secured to the support block 72 provides an electronic signal representative of the linear position of the lens 68 as it traverses the periphery of the breast at each angular position of the orbit. The linear encoder 78 is designed to produce a signal in proportion to the linear distance traversed by the lens 68. As the lens 68 and the associated structure are orbited around the breast 6, the position of the lens 68 at each pre-determined angular position around a complete circle is determined by the linear displacement of the support block 72, which is detected by the linear encoder 78. A person of ordinary skill in the art will understand that at each angular position of the orbit, the lateral distance of the lens 68 from a known reference point is uniquely determined from the lateral displacement of the support block 72. A trace of the periphery of the breast 6 is thus determined for each complete orbit of the lens 68.

Determination of the map of the perimeter of the scanned object has several useful applications. The perimeter map is centered on the axis of rotation of the orbit around the scanned object. Since the location of the laser beam is known as a function of the perimeter at each position in the orbit of the scanned object, the optical path length from the point at which the laser beam impinges on the scanned object to each point on the perimeter is also known.

Knowledge of the optical path length and the index of refraction of the material of the scanned object provides knowledge of the optical delay encountered by photons traveling within the scanned object. This optical delay parameter is useful in time-gated studies where only a portion of the photons emerging from the scanned object are desired as acquired data.

Knowledge of the optical path length also provides the means for adjusting parameters in a data acquisition method. For example, knowledge of the optical path length provides an indication of the optical attenuation through the scanned object.

Knowledge of the optical attenuation could be used to control the power of the laser or gains of the detectors. Because the knowledge of the perimeter of a scanned object is known for all positions of the orbit, an adaptive data acquisition scheme is possible and could be used to optimize data acquisition parameters.

Use of the perimeter data of the scanned object is discussed in provisional applications Ser. Nos. 60/032,590, 60/032,592, 60/032,594 and 60/032,593, all filed on Nov. 29, 1996, which are hereby incorporated by reference.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. An apparatus for determining the perimeter of an object being scanned, comprising:

a) a plate for orbiting around the object being scanned;

b) a movable arm (operably) secured to said plate, said arm for following the surface of the object being scanned as said plate is orbited around the object;

c) said arm having one end for maintaining contact with the surface as said plate is orbited around the object; and d) an encoder connected to said arm for determining the movement of said arm as said plate is orbited around the object.

2. An apparatus as in claim 1, wherein:

a) said arm is laterally slidable; and b) said encoder is a linear encoder.

3. An apparatus as in claim 1, wherein:

a) said arm is pivotable; and b) said encoder is a rotary encoder.

4. An apparatus as in claim 1, wherein:

a) said one end includes an opaque cup for entrapping reflected light off the surface of the object being scanned.

5. An apparatus as in claim 4, wherein:

a) said cup is pivotably connected to said one end.

6. An apparatus as in claim 1, wherein:

a) said plate is ring-shaped having an opening for suspending in said opening the object being scanned.

7. An apparatus as in claim 1, wherein:

a) said arm is pivotable; and b) said arm includes a weight that exerts a torque to bias said arm toward the object being scanned when said plate is orbited around the object.

8. An apparatus as in claim 7, wherein;
   a) said arm includes a spring that pulls said arm away from the object being scanned when said plate is at rest.

9. An apparatus for bringing a source of laser beam to the surface of an object being scanned, comprising:
   a) a plate for orbiting around the object being scanned;
   b) a movable support secured to said plate;
   c) a fiber optic cable supported by said movable support, said fiber optic cable for being connected to a source of laser beam;
   d) a lens coupled to one end of said fiber optic cable, said lens for being in intimate contact with the surface of the object being scanned as said plate is orbited around the object; and
   e) said movable support including a spring for permitting said lens to follow the perimeter of the surface of the object being scanned while said plate is orbited around the object.

10. An apparatus as in claim 9, wherein:
    a) said movable support is laterally slidable.

11. An apparatus as in claim 9, wherein:
    a) said movable support is pivotable.

12. An apparatus as in claim 9, wherein:
    a) said lens is spherical.

13. An apparatus as in claim 9, wherein:
    a) said plate is ring-shaped having an opening for suspending in said opening the object being scanned.

14. An apparatus for bringing a source of laser beam to the surface of an object being scanned, comprising:
    a) a plate for orbiting around the object being scanned;
    b) a movable arm secured to said plate, said arm for following the surface of the object being scanned as said plate is orbited around the object;
    c) said arm having one end for maintaining contact with the surface as said plate is orbited around the object; and
    d) a fiber optic cable connected to a laser source, said optic fiber being carried by said arm.

15. An apparatus as in claim 14, wherein:
    a) said one end of said arm includes a lens for being in contact with the surface.

16. An apparatus as in claim 15, wherein:
    a) said lens is spherical.

* * * * *

UNITED STATES PATENT AND TRADEMARK OFFICE
CERTIFICATE OF CORRECTION

PATENT NO. : 6,029,077
DATED : February 22, 2000
INVENTOR(S) : Robert H. WAKE et al.

It is certified that error appears in the above-indentified patent and that said Letters Patent is hereby corrected as shown below:

In col. 6, line 37, please delete "(operably)".

Signed and Sealed this

Fourteenth Day of November, 2000

Attest:

Q. TODD DICKINSON

*Attesting Officer*         *Director of Patents and Trademarks*